US009696269B2

(12) United States Patent
Fordham et al.

(10) Patent No.: US 9,696,269 B2
(45) Date of Patent: Jul. 4, 2017

(54) NMR ANALYSIS OF A CORE SAMPLE EMPLOYING AN OPEN PERMANENT MAGNET REMOVABLE FROM A CORE HOLDER

(75) Inventors: Edmund J. Fordham, Cambridge (GB); Jonathan Mitchell, Great Cambourne (GB)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 211 days.

(21) Appl. No.: 14/362,401

(22) PCT Filed: May 15, 2012

(86) PCT No.: PCT/IB2012/052439
§ 371 (c)(1),
(2), (4) Date: Jun. 10, 2014

(87) PCT Pub. No.: WO2013/171544
PCT Pub. Date: Nov. 21, 2013

(65) Prior Publication Data
US 2015/0061670 A1    Mar. 5, 2015

(51) Int. Cl.
*G01V 3/00*      (2006.01)
*G01N 24/08*     (2006.01)
(Continued)

(52) U.S. Cl.
CPC ............. *G01N 24/081* (2013.01); *G01N 1/00* (2013.01); *G01R 33/305* (2013.01);
(Continued)

(58) Field of Classification Search
USPC ......................................................... 324/309
See application file for complete search history.

(56) References Cited

U.S. PATENT DOCUMENTS 2,345,935 A    4/1942   Hassler
4,769,602 A    9/1988   Vinegar et al.
(Continued)

OTHER PUBLICATIONS

C.W. Windt, et al., "A Portable Halbach magnet that can be opened and closed without force: the NMR-CUFF," Journal of Magnetic Resonance, 208(1), Jan. 2011, pp. 27-33.
(Continued)

*Primary Examiner* — Rodney Fuller

(57) ABSTRACT

An apparatus and method for NMR analysis of a plurality of core samples includes a core holder (11) that holds a core sample under pressurized conditions. A radio frequency coil (51) disposed about the core holder (11) generates a pulsed-mode magnetic field component over a sample volume occupied by the core sample. A support structure is removably secured to the respective core holder. A permanent magnet (65A, 65B) has an open configuration such that it is removably disposed into a position within the support structure about the radio frequency coil and the core holder. The open configuration allows the same permanent magnet to be used for NMR analysis of a plurality of core samples without the need for depressurizing the respective core holder and disassembling the core holder and corresponding load frame for each core sample. It also allows multiple core samples to be prepared for NMR analysis while separated from the NMR measurement apparatus.

21 Claims, 9 Drawing Sheets

(51) Int. Cl.
*G01R 33/30* (2006.01)
*G01R 33/383* (2006.01)
*G01N 1/00* (2006.01)
*G01R 33/38* (2006.01)
*G01V 3/32* (2006.01)

(52) U.S. Cl.
CPC ........ *G01R 33/383* (2013.01); *G01R 33/3806* (2013.01); *G01V 3/32* (2013.01)

(56) References Cited

U.S. PATENT DOCUMENTS

| | | | | |
|---|---|---|---|---|
| 4,868,751 | A * | 9/1989 | Dogru | G01N 15/08 702/12 |
| 5,315,276 | A | 5/1994 | Huson et al. | |
| 5,565,834 | A | 10/1996 | Hanley et al. | |
| 6,570,382 | B1 | 5/2003 | Hurlimann et al. | |
| 6,577,125 | B2 * | 6/2003 | Prammer | G01V 3/32 324/303 |
| 6,842,002 | B2 | 1/2005 | Cheng et al. | |
| 6,960,913 | B2 | 11/2005 | Heaton | |
| 7,053,611 | B2 | 5/2006 | Freedman | |
| 2003/0011455 | A1 * | 1/2003 | Wakuda | G01R 33/3806 335/299 |
| 2006/0116828 | A1 * | 6/2006 | Chen | G01N 24/08 702/22 |
| 2008/0150542 | A1 | 6/2008 | Sapp et al. | |
| 2009/0256562 | A1 * | 10/2009 | Gao | G01N 24/08 324/308 |
| 2009/0289632 | A1 | 11/2009 | Bluemler et al. | |
| 2010/0126266 | A1 | 5/2010 | Coenen | |
| 2011/0050223 | A1 | 3/2011 | Balcom et al. | |

OTHER PUBLICATIONS

P.M. Singer, et al., "Low magnetic fields for flow propagators in permeable rocks," Journal of Magnetic Resonance, vol. 183, pp. 167-177, 2006.

M. Helbek, et al, "Self-diffusion coefficients of methane or ethane mixtures with hydrocarbons at high pressure by NMR," Journal Chemical & Engineering Data, vol. 41, pp. 598-603, 1996.

D.I. Hoult, et al., "The signal-to-noise ratio of the nuclear magnetic resonance experiment," Journal of Magnetic Resonance, vol. 24, pp. 71-85, 1976.

J. Arnold, et al, "Porosity and permeability from mobile nmr core-scanning," Petrophys., vol. 47, pp. 306-314, 2006.

S. Anferova, "Improved Halbach sensor for NMR scanning of drill cores," Magnetic Resonance Imaging, vol. 25, pp. 474-480, 2007.

K. Halbach, "Design of permanent multipole mangnets with oriented rare earth cobalt material," Nuclear Instruments and Methods, vol. 169, pp. 1-10, 1980.

H. Raich, et al, "Design and construction of a dipolar Halbach array with a homogeneous field from identical bar-magnets: NMR mandhalas," Magnetic Resonance Engineering, vol. 23B, pp. 16-25, 2004.

C. Bauer, et al., "Design of a permanent magnet with a mechanical sweep suitable for variable-temperature continuous-wave and pulsed EPR spectroscopy," Journal of Magnetic Resonance, vol. 198, pp. 222-227, 2009.

Hui Han, et al, "High pressure magnetic resonance imaging with metallic vessels," Journal of Magnetic Resonance, vol. 213, No. 1, Sep. 10, 2011, pp. 90-97.

Temco, Inc., "HCH Series—Biaxial Core Holders", 4 pages https://web.archive.org/web/20170219155627 /http://public.hofstragroup.com/3021.pdf Feb. 19, 2017.

Temco, Inc., NMR/MRI Microwave Core Holder, 2 pages https://web.archive.org/web/20130601113131/http://www.corelab.com/cli/core-holders/nmr-mr-microwave-core-holder-fch-series, dated Jun. 1, 2013.

* cited by examiner

NMR ANALYSIS OF A CORE SAMPLE EMPLOYING AN OPEN PERMANENT MAGNET REMOVABLE FROM A CORE HOLDER

BACKGROUND

Field of the Invention

The present invention relates to nuclear magnetic resonance (NMR) analysis and more specifically to enclosures for holding subterranean core samples suitable for NMR analysis of the subterranean core samples.

Description of Related Art

NMR analysis of rock core samples extracted from subterranean wells (hereinafter referred to as "rock core samples" or "core samples") is routinely performed in laboratories in order to examine the T2 relaxation time distribution and other properties of the rock and bound fluids in the respective core samples. These measured properties can be interpreted to give a wide range of information on the pore size distributions and geometry, effective and free-fluid porosities, fluid saturations and distributions, capillary-bound water, permeability, oil viscosity, free fluids, mobile oil, gas and water, clay bound water, and producible fluids and fluid types. Those familiar with the art recognize the significance of these measurements.

NMR analysis of a core sample can be performed while injecting fluids (such as water or surfactant solutions) into the core sample with the use of an appropriate NMR compatible core holder with flow-through capability. This configuration allows for monitoring the recovery of oil from the core sample due to such injection. Whilst such analysis can be performed at realistic reservoir conditions (temperature and pressure), it is difficult to attain in situ analysis of live oil (i.e., oil containing volatile hydrocarbons, gaseous hydrocarbons (e.g. methane) dissolved in solution, and other gases such as $H_2S$ and $CO_2$ in solution) because the system will out-gas at reduced pressures (relative to the reservoir). This can prevent a direct comparison between laboratory-scale measurements and data obtained from NMR well logging tools.

Additionally, core samples are often cleaned via processes such as Soxhlet extraction, which alters the wettability of the core sample. It is therefore necessary to restore the natural wettability state prior to the NMR analysis, and this is achieved typically by saturating the core sample with dead oil and then ageing it at an elevated temperature and pressure for several weeks.

If a core sample is to be tested with live oil at reservoir conditions, the core sample must be saturated at elevated pressure to preserve the dissolved gases. It is then necessary to maintain this pressure during the NMR experiments. In the current state of the art, the core sample is loaded into a core holder. An exemplary flow-thru Hassler-type biaxial core holder 11 is shown in FIG. 1. The Hassler-type biaxial core holder is a core holder that applies common radial and axial pressure to the core sample. The core holder 11 includes a tubular vessel 13 that supports an internal flexible sleeve 15 that floats inside the tubular vessel 13 with an annular gap 17 therebetween. Both the tubular vessel 13 and the flexible sleeve 15 are constructed from a material that is non-magnetic and substantially transparent to the radio frequency (RF) radiation employed for NMR analysis. For example, the tubular vessel 13 can be constructed from a glass fiber-reinforced plastic using an epoxy resin or PEEK (polyetheretherketone) as the matrix. The flexible sleeve 15 can be constructed from perfluorinated rubber such as Chemraz®, available from Greene, Tweed and Company of Kulpsville, Pa., USA, or Kalrez®, available from E. I. du Pont de Nemours and Company of Wilmington, Del., USA, or partially-fluorinated rubber such as Viton®, also available from E. I. du Pont de Nemours and Company. The interior space of the flexible sleeve 15 receives the core sample 19. The annular gap 17 defines a radial pressure chamber for applying radial pressure to the core sample 19 via the annular wall of the flexible sleeve 15. The opposed ends of the flexible sleeve 15 are sealed by corresponding end platens 21A, 21B. End caps 23A, 23B are secured to opposed ends of the tubular vessel 13. An interior space 25 between the end cap 23A and the end platen 21A on one end of the flexible sleeve 15 defines an axial pressure chamber for applying axial pressure to the core sample 19 via the end platen 21A. One or more pressure ports (for example, two shown as 27A, 27B) are provided on the annular wall of the tubular vessel 13. The pressure port(s) are fluidly coupled to both the radial pressure chamber 17 and the axial pressure chamber 25 by fluid passageways 29A, 29B. The pressure port(s) 27A, 27B receive pressurized fluid that is substantially transparent to the RF radiation employed for NMR analysis (such as the any of the Flourinert® family of per-fluorinated hydrocarbons available from 3M Company of Minneapolis, Minn., USA). The pressurized fluid fills the radial pressure chamber 17 and the axial pressure chamber 25 to apply both radial and axial pressure to the core sample 19. The radial pressure prevents out-gassing and fluid flow around the core sample 19 during the acquisition of NMR measurements of the core sample 19. The temperature of the core sample 19 is controlled by the temperature of the pressurized fluid supplied to the pressure port(s). Pressure and temperature is typically regulated by a reservoir of pressurized fluid that is fluidly coupled to the pressure port(s). One end cap 23A includes a fluid inlet port 31A that communicates with a fluid inlet path 33A extending through the adjacent end platen 21A and into the interior space of the flexible sleeve 15 for the supply of fluid (such as oil) to the core sample 19. The opposite end cap 23B includes a fluid outlet port 31B that communicates with a fluid outlet path 33B extending through the adjacent end platen 21B and into the interior space of the flexible sleeve 15 for the discharge of fluid from the core sample 19. The fluid inlet port 31A and the fluid outlet port 31B allow the core sample 19 to be prepared for NMR analysis. Such preparation can involve saturating the core sample 19 with oil at the required conditions for live oil studies. Such prior art flow-thru Hassler-type biaxial core holders are sold commercially by ErgoTech Limited of Conwy, United Kingdom.

The core holder can be confined by a load frame and is surrounded by a permanent magnet (four iron yoke pillars supporting two opposed magnetic poles) while the core is prepared. The permanent magnet is used for NMR analysis and remains in position surrounding the core holder during the preparation of the core sample and during the NMR analysis.

SUMMARY

The present application includes an apparatus (and corresponding method) for NMR analysis of a plurality of core samples. Core holders are provided for holding each respective core sample under pressurized conditions. A radio frequency coil is disposed about a portion of the respective core holder. The radio frequency coil is used to generate a pulsed-mode magnetic field component over a sample volume occupied by the core sample. A support structure is removably secured to the respective core holder. The support structure provides resistance to forces resulting from the pressurized conditions of the core holder. The support structure allows for access to interior space surrounding the core holder and the radio frequency coil disposed thereabout. A permanent magnet (and possibly a gradient coil array) is removably disposed into a position within the support structure about the radio frequency coil and the core holder. The permanent magnet has an open configuration that allows the permanent magnet to be removably disposed within the support structure about the radio frequency coil and the portion of the core holder without the need for depressurization of the core holder and detachment of the support structure from the core holder. The permanent magnet applies a static magnetic field component to the sample volume for NMR analysis of the core sample. The open configuration of the permanent magnet allows the same permanent magnet (and possibly the gradient coil array supported thereon) to be used for NMR analysis of a plurality of core samples without the need for depressurizing the respective core holder and disassembling the respective core holder and corresponding load frame for each core sample.

The apparatus (and corresponding method) of the present application allows multiple core samples to be prepared for NMR analysis (such as by ageing with oil under reservoir conditions) with the samples separated from the permanent magnet and the NMR measurement apparatus. After the preparation of a respective core sample is complete, the permanent magnet (and possibly a gradient coil supported thereon) can be removably disposed into a position within the corresponding support structure about the radio frequency coil and the respective core holder without the need for depressurizing the respective core holder and disassembling the respective core holder and corresponding load frame for each core sample. The radio frequency coil (and possibly the gradient coil) can then be connected to the NMR measurement apparatus for NMR analysis of the respective core sample. The core sample can be pressurized at reservoir conditions during the NMR analysis. After such NMR analysis is complete for the respective core sample, the permanent magnet (and possibly a gradient coil supported thereon) can be removed from its position within the corresponding support structure about the radio frequency coil and the respective core holder without the need for depressurizing the respective core holder and disassembling the respective core holder and corresponding load frame for the respective core sample. The process can then be repeated for NMR analysis of additional core samples where the same permanent magnet is removably disposed into a position within the corresponding support structure about the radio frequency coil and the respective core holder of the additional samples without the need for depressurizing the respective core holder and disassembling the respective core holder and corresponding load frame for each core sample.

In one embodiment of the present application, the permanent magnet includes a U-shaped or C-shaped body that supports two magnet poles, where the U-shaped or C-shaped body defines the open configuration that allows the permanent magnet (and possibly the gradient coil array supported thereon) to be used for NMR analysis of a plurality of core samples without the need for depressurizing the respective core holder and disassembling the respective core holder and corresponding load frame for each core sample.

In another embodiment of the present application, the permanent magnet includes a part that is removably secured to a U-shaped or C-shaped body to reconfigure the permanent magnet into a closed configuration.

In yet another embodiment of the present application, the permanent magnet comprises two cylindrical Halbach-type arrays that are arranged in a concentric configuration during use. The two cylindrical Halbach-type arrays each have two semi-cylindrical portions that are coupled together via a hinge interface. Pivoting movement of the two semi-cylindrical portions about the hinge interface permits the two cylindrical Halbach-type arrays to be arranged in the open configuration that allows the two cylindrical Halbach-type arrays (and possibly a gradient coil array supported on the inner array) to be used for NMR analysis of a plurality of core samples without the need for depressurizing the respective core holder and disassembling the respective core holder and corresponding load frame for each core sample.

DETAILED DESCRIPTION

Figure 1:
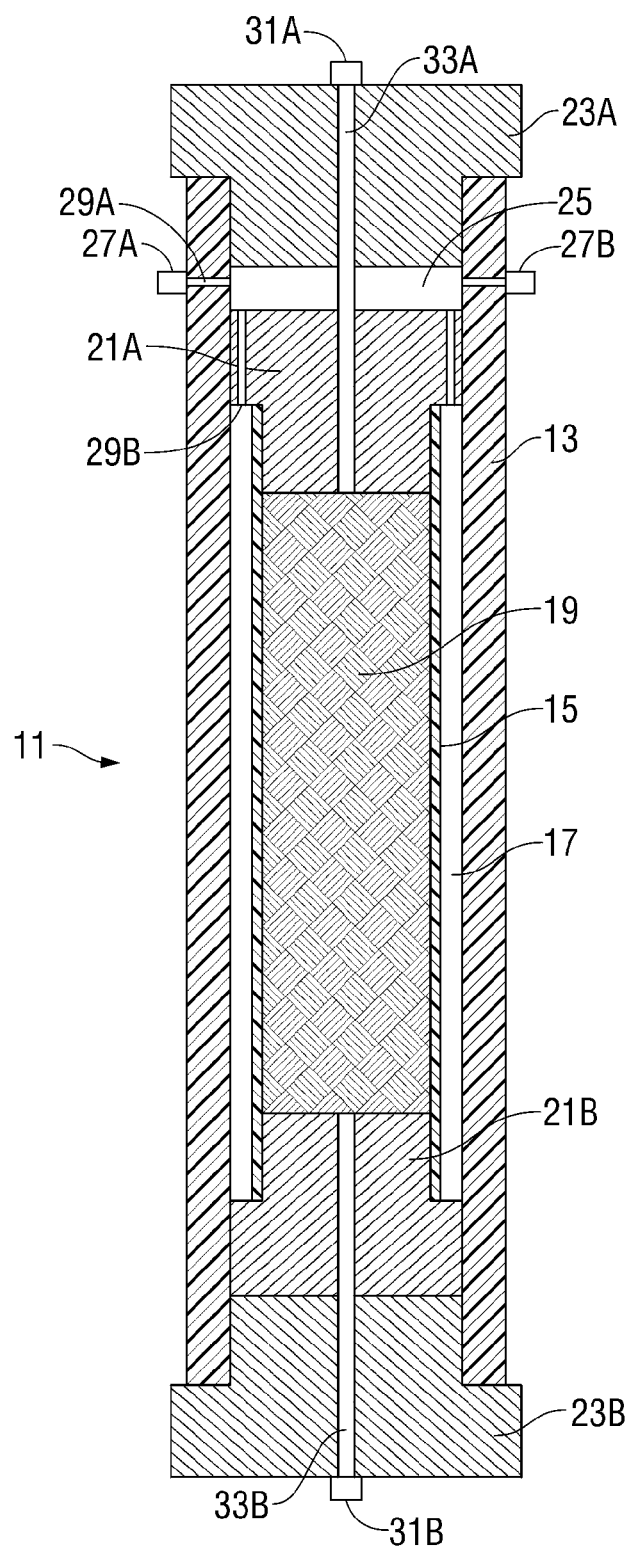
FIG. 1 is a schematic cross-sectional diagram of a flow-thru Hassler-type biaxial core holder of the prior art.

The present application employs a flow-through core holder to prepare a core sample for NMR analysis. An example of a flow-through Hassler-type biaxial core holder is described above with respect to FIG. 1. The NMR analysis of the core sample is based upon well-known principles that have become an important tool in formation evaluation. Such NMR analysis relies upon the fact that the nuclei of many chemical elements have angular momentum ("spin") and a magnetic moment. In an externally applied static magnetic field $B_0$, the spins of nuclei align themselves along the direction of the static magnetic field $B_0$. This equilibrium situation can be disturbed by a pulse of an oscillating magnetic field $B_1$ that tips the spins away from the direction of the static magnetic field $B_0$. For example, if a pulse of alternating current having a frequency f is passed through a radio frequency antenna coil producing the oscillating polarizing magnetic field $B_1$ perpendicular to the static magnetic field $B_0$, a population of nuclei precessing at the Larmor frequency equal to f align at angle θ relative to the $B_0$ direction. At the end of the pulse, when the polarizing magnetic field $B_1$ is removed, the aligned nuclei experience a perpendicular torque, and precess about the $B_0$ vector. After a characteristic time called the longitudinal or spin-lattice relaxation time $T_1$, the nuclei relax to the thermal equilibrium, where a weighted percentage of the nuclei are aligned in the $B_0$ direction. The angle θ is given by θ=γ$B_1 t_p$/2, where γ is the gyromagnetic ratio, $B_1$ is the linearly polarized oscillating field strength, and $t_p$ is the duration of the pulse. Pulses that produce an angle θ of ninety degrees (referred to as a "90-degree pulse") are common.

Also associated with the spin of molecular nuclei is a second relaxation time, $T_2$, called the spin-spin relaxation time. At the end of a 90-degree pulse, all the spins are pointed in a common direction perpendicular, or transverse, to the $B_0$ direction, and they all precess at the Larmor frequency. However, because of small fluctuations in the static field induced by other spins, paramagnetic impurities and the inhomogeneity of the static $B_0$ field, the spins precess at slightly different frequencies, and the transverse magnetization dephases with a time constant referred to as the spin-spin relaxation time $T_2$.

A standard technique for measuring the spin-spin relaxation time $T_2$ utilizes an RF pulse sequence known as the CPMG (Carr-Purcell-Meiboom-Gill) sequence. As is well known, after a wait time that precedes each pulse sequence, a 90-degree RF pulse is emitted, which causes the spins to start precessing in the transverse plane. After a delay, an initial 180-degree RF pulse is emitted. The initial 180-degree pulse causes the spins, which are dephasing in the transverse plane, to reverse direction and to refocus and subsequently cause an initial spin echo to appear. A second 180-degree refocusing RF pulse can be emitted, which subsequently causes a second spin echo to appear. Thereafter, a series of 180-degree RF pulses separated by a short time delay is emitted. This series of 180-degree pulses repeatedly reverse the spins, causing a series of "spin echoes" to appear. The train of spin echoes is measured and processed to determine the spin-spin relaxation time $T_2$.

In a uniform static magnetic field, each spin will experience the same magnetic field strength regardless of its position within the static field, and diffusion will not contribute to the observed spin-spin relaxation time $T_2$. However, in the magnetic field gradient of the inhomogeneous static magnetic field $B_0$, each spin will experience different magnetic field strengths as it diffuses through the static field. The Larmor frequencies of the diffusing spins become time dependent, and the 180-degree pulses cannot refocus the spins completely, leading to an additional decay. This additional decay contributes to the observed spin-spin relaxation time $T_2$ and is dependent on the diffusion coefficient D of the fluid, the magnitude and duration of the magnetic field gradient, and the magnitude of the static magnetic field. As the diffusion coefficient provides an indication of fluid type, measurement of the diffusion effects on observed spin-spin relaxation time $T_2$ can be used as the basis for determining the types of fluids in a hydrocarbon formation.

NMR analysis utilizing inhomogeneous static fields in conjunction with diffusion editing by either stimulated echoes (STE) or Hahn echoes (HE) followed by a modified CPMG pulse train is also standard practice. Examples of such NMR analysis are set forth in U.S. Pat. No. 6,570,382.

NMR analysis measures the spin echo amplitude for one or more NMR sequences. From these measurements, the diffusion coefficient D, as well as other fluid properties of the sample under evaluation can be derived. The NMR measurements thus obtained are "diffusion encoded" and can be inverted to produce a multi-dimensional distribution function relating to fluid properties of the tested sample. The multi-dimensional distribution can be a two dimensional (2-D) distribution function $f(D,T_2)$ relating the diffusion coefficient D to the spin-spin ($T_2$) relaxation times of the sample, a 2-D distribution function $f(D,T_1)$ relating the diffusion coefficient D to the spin-lattice relaxation time $T_1$ of the sample, or a three-dimensional (3-D) distribution function $f(D, T_1, T_2)$ relating the diffusion coefficient D to the spin-lattice relaxation time $T_1$ and the spin-spin relaxation time $T_2$ of the sample. Examples of such inversion techniques are described in detail in U.S. Pat. Nos. 6,570,382; 6,960,913; and 7,053,611. For example, the multi-dimensional distribution function can be a 2-D distribution function $f(D,T_2)$ relating the diffusion coefficient D to the spin-spin ($T_2$) relaxation times of the sample. For an oil-water sample, the function $f(D,T_2)$ can be used to estimate the relative volumes of oil and water, oil viscosity, molecular composition of the oil, and gas-oil ratio.

Figure 2:
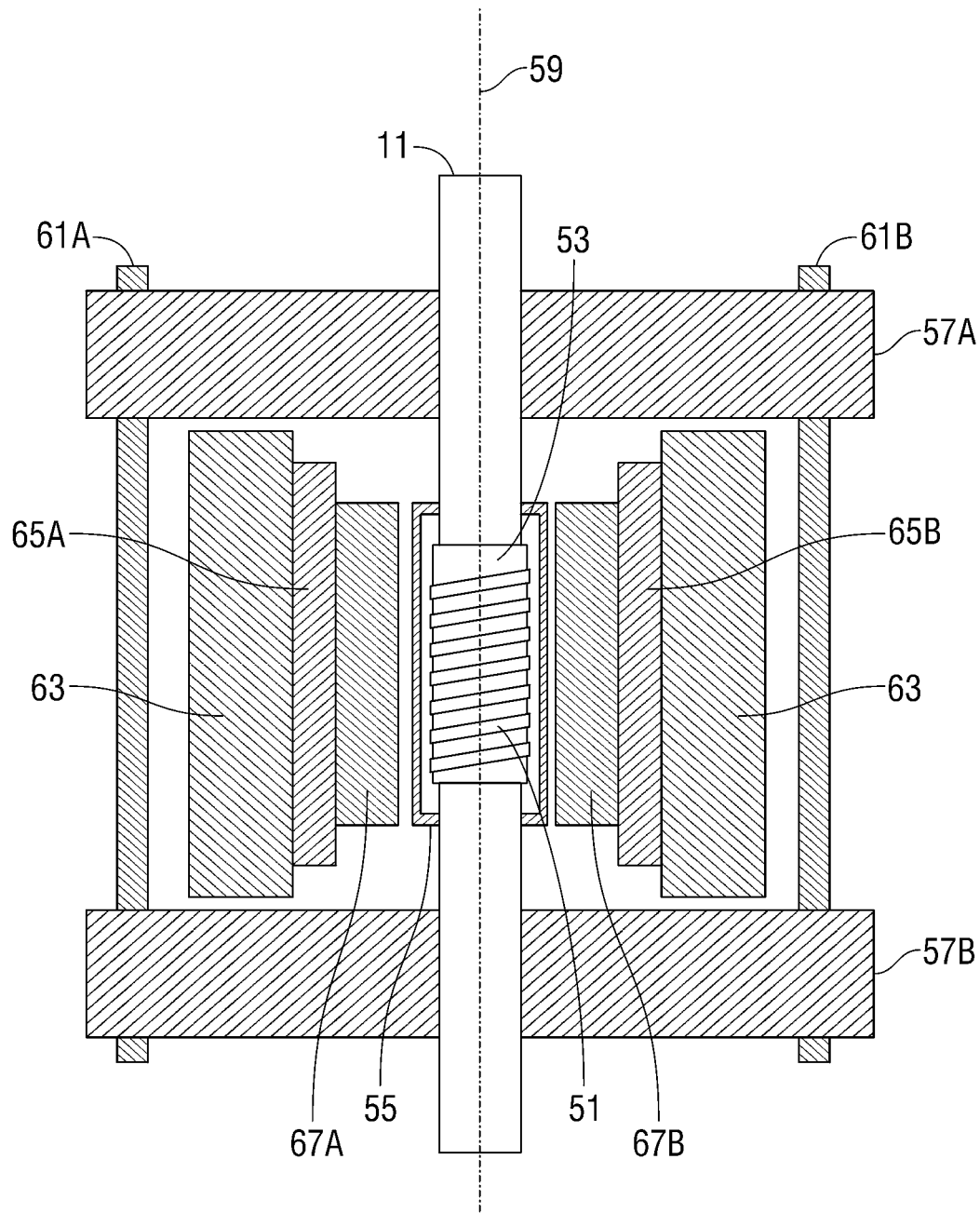
FIG. 2 is a schematic cross-sectional diagram of an apparatus including a load frame assembly that is secured to a core holder; the load frame assembly provides resistance to forces resulting from the pressurized conditions of the core holder and allows for access to interior space surrounding the core holder and a radio frequency coil disposed thereabout; a permanent magnet and a gradient coil array is removably disposed in a position within the load frame assembly about the radio frequency coil and the core holder.

For NMR, a radio frequency excitation and detection coil 51 is wound around a hollow cylindrical former 53 that defines a lumen that receives the central portion of the tubular vessel 13 of the core holder 11 as shown in FIG. 2. The former 53 and the coil 51 can be housed within an aluminum enclosure 55 to provide a screen against external radio frequency noise sources. To allow confining pressures of the core sample to be achieved at levels corresponding to high pressure reservoir conditions (e.g., pressures in excess of about 5000 psi), a load frame is placed around the tubular vessel 13 of the core holder 11. The load frame includes two aluminum cross-beams 57A, 57B that extend transverse to the central axis 59 of the tubular vessel 13. The two cross-beams 57A, 57B are supported by rods (for example, two shown as 61A, 61B) that are fixed in position offset from one another and extend parallel to the central axis 59 of the core holder 11. The stresses associated with the confining pressures of the core holder 11 are distributed through the cross-beams 57A, 57B. More specifically, the radial stresses associated with the confining pressure are distributed by contact between the outer wall of the core holder 11 and the cross-beams 57A, 57B. The rods 61A, 61B define openings that allow for access to internal space that surrounds the central portion of the vessel 13 of the core holder 11 and the radio frequency coil 51 disposed thereabout.

A permanent magnet (realized by an iron yoke 63 and opposed magnet poles 65A, 65B) is supported within the load frame as shown in FIG. 2. The permanent magnet produces a homogeneous static magnetic field $B_0$ in the volume occupied by the core sample (this is referred to as the "sample volume"). In the preferred embodiment, the permanent magnet produces a static magnetic field $B_0$ on the order of 42 mT (proton frequency of 2 MHz). Lower strength and higher strength fields can be used. Lower strength fields suffer from decreases in signal-to-noise ratio. High strength fields can provide improved signal-to-noise ratio, but the measured NMR properties can be significantly different from those measured by modern NMR logging tools. The iron yoke 63 serves two main functions, namely to provide a low reluctance return path for the magnetic field and to provide mechanical support for the opposed magnet poles 65A, 65B. The magnet poles 65A, 65B are constructed from a permanently magnetized material, such as neodymium iron boron (NdFeB) or samarium cobalt. Additional permanent magnets can be supported by yoke in order to improve the homogeneity of the static magnetic field $B_0$ over the sample volume.

A gradient coil array 67A, 67B is disposed between the permanent magnet and the sample volume. The radio frequency coil 51 transmits pulses of an oscillating magnetic field $B_1$ across the sample volume. The magnetic moment of the magnetic field $B_1$ is substantially perpendicular to the static magnetic field $B_0$. The gradient coil array 67A, 67B provides a spatial variation in the static magnetic field $B_0$ across the sample volume (for example, it can transmit a pulsed-mode magnetic field gradient across the sample volume, which can modify the homogeneous static magnetic field $B_0$ along any coordinate (x, y, z, r) in the sample volume).

Figure 3:
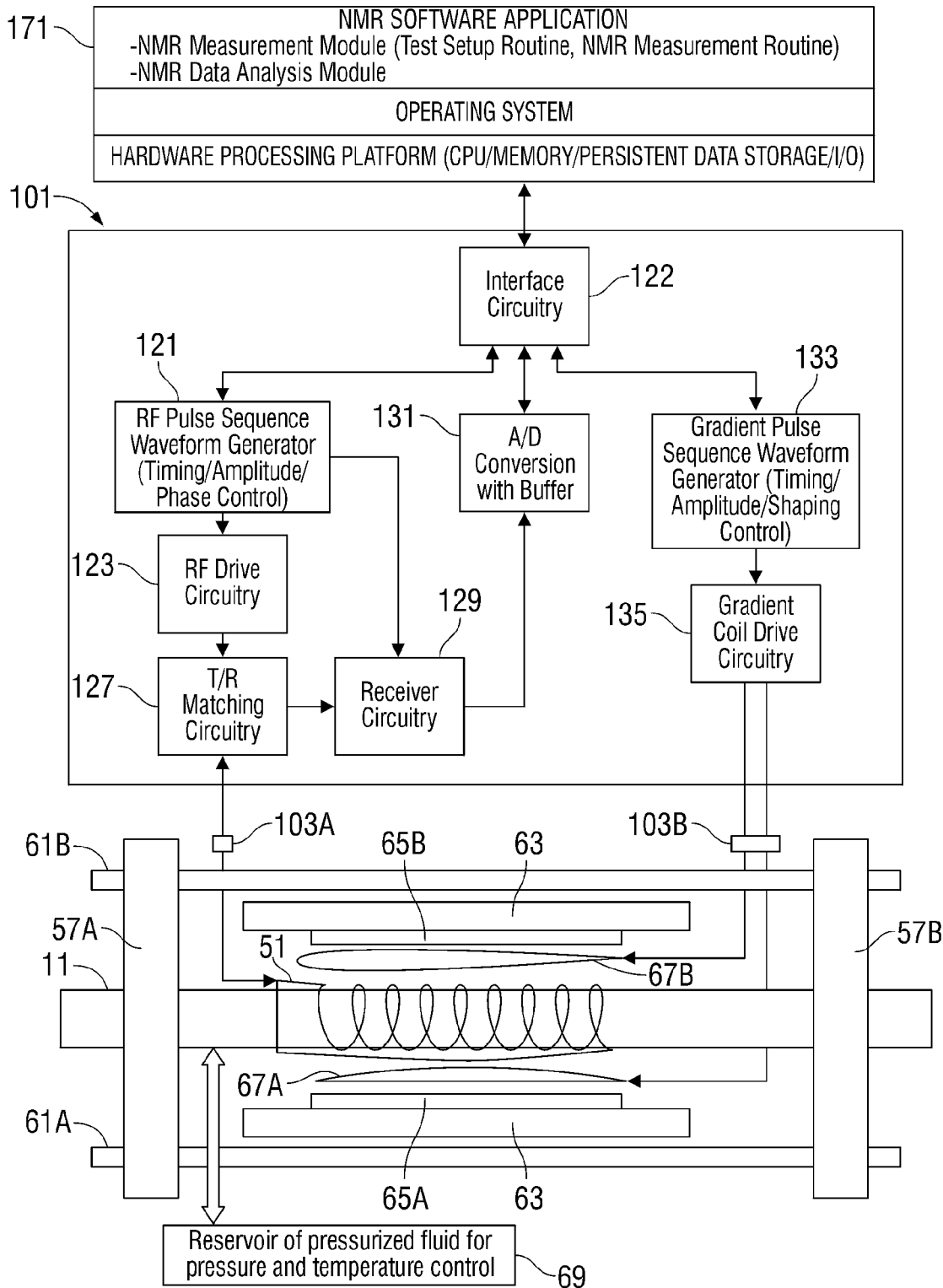
FIG. 3 is a schematic block diagram of an NMR measurement apparatus that is electrically connected to the radio frequency coil and gradient coil array of the apparatus of FIG. 2 in order to carry out NMR measurements of the core sample held within the core holder of the apparatus of FIG. 2.

As shown in FIG. 3, an NMR instrument housing 101 is provided that contains electronic circuitry that is detachably connected via respective connectors 103A, 103B to the radio frequency coil 51 and gradient coil array 67A, 67B of the apparatus of FIG. 2 to carry out NMR measurements on a core sample of interest supported by the apparatus of FIG. 2 in the sample volume. The electronic circuitry preferably operates in three modes: transmitting mode, damping mode, and receiving mode. In the transmitting mode, the radio frequency coil 51 is excited such that it radiates a pulse of an oscillating magnetic field $B_1$ across the sample volume. The pulse of oscillating magnetic field $B_1$ resonates nuclear spins in the core sample of interest disposed in the sample volume. Between certain pulses of the oscillating magnetic field $B_1$ produced in the transmit mode, the receive mode is carried out using the radio frequency coil 51 to receive oscillating magnetic signals of nuclear spin precession (also referred to as "spin echoes") radiating from the core sample of interest disposed in the sample volume. The damping mode is carried out between the transmit mode and receive mode in order to limit ringing of the radio frequency coil 51 at the end of the pulse of the oscillating magnetic field $B_1$. The electronic circuitry also operates to excite the gradient coil array 67A, 67B such that the gradient coil array radiates the pulsed-mode magnetic field gradient $B_{PFG}$ across the sample volume as required for the analysis.

A reservoir 69 of pressurized fluid is fluid coupled to the pressure ports of the core holder 11. The pressure and temperature of the pressurized fluid of the reservoir can be controlled at desired levels representative of reservoir conditions in order to control the axial and radial pressures applied to the core sample of interest as well as the temperature of the core sample under test during NMR measurements of the core sample of interest.

In one embodiment, the electronic circuitry of the instrument housing 101 includes a circuit block 121 for generating RF pulse sequence waveforms that excite the pulses of oscillating magnetic field $B_1$ across the sample volume. The parameters of the RF pulse sequence waveforms are preferably controlled by control signals supplied to circuit block 121 from computer 171 via interface circuitry 122. The RF pulse sequence waveforms generated by circuit block 121 are supplied to an RF drive circuitry 123 that amplifies the RF pulse sequence waveform to suitable power levels for supply to the radio frequency coil 51 in the transmit mode such that the radio frequency coil 51 radiates pulses of oscillating magnetic field $B_1$ oscillating at the Larmor frequency of the nucleus of interest. The T/R matching circuitry 127 provides an impedance that matches the input impedance of the radio frequency coil 51 in the transmit mode in order maximize power transmission to the radio frequency coil 51, and also provides an impedance that matches the input impedance of the receiver circuitry 129 in the receive mode in order to minimize noise. The T/R matching circuitry 127 also provides impedance that critically dampens the radio frequency coil 51 in the damping mode in order to limit ringing of the radio frequency coil 51 at the end of the pulse of the oscillating magnetic field $B_1$. In the receive mode, the receiver circuitry 129 amplifies the signals captured by the radio frequency coil 51 and supplied by the T/R matching circuitry 127, and utilizes a reference signal supplied by the circuit block 121 (this reference signal corresponds to the frequency of interest) and the amplified signal to obtain a measured NMR resonance signal at the frequency of interest from the sample volume. The measured NMR resonance signal is output to an analog-to-digital (A/D) converter 131 for sampling and conversion into digital form. The digital data is buffered and forwarded to the computer 171 via interface circuitry 122 for further use and analysis.

The electronic circuitry of the instrument housing 101 also includes a circuit block 133 for generating gradient pulse sequence waveforms that produce the pulsed-mode magnetic field gradient $B_{PFG}$ across the sample volume. The parameters of the gradient pulse sequence waveforms are preferably controlled by control signals supplied to circuit block 133 from computer 171 via interface circuitry 122. The gradient pulse sequence waveforms generated by circuit block 133 are supplied to gradient coil drive circuitry 135, which operates to amplify the gradient pulse sequence waveform generated by circuit block 133 to suitable power levels for supply to the gradient coil array 67A, 67B such that the gradient coil array 67A, 67B radiates pulses of the pulsed-mode magnetic field gradient $B_{PFG}$ across the sample volume.

The computer 171 includes a hardware processing platform that includes at least one central processing unit, memory, persistent data storage (e.g., a hard disk drive or optical disk), I/O functionality, and other functionality as is well known in the data processing arts. The persistent data storage stores an operating system and a software application (a programmed sequence of instructions) that are both loaded into memory for execution by the central processing unit(s) of the platform as is well known. In an exemplary embodiment, the computer 171 is realized by a commercially available workstation that interfaces to the instrument housing 101 by a suitable interface, such as a USB or 1394 data link. The software application embodies an NMR measurement module and an NMR data analysis module that carry out the laboratory NMR measurement and analysis of the core sample of interest. The NMR measurement module performs NMR measurements on the core sample of interest. The NMR measurements are derived from operation of a test setup routine and NMR measurement routine.

The test setup routine interfaces with the waveform generator circuit block 121 to supply the necessary parameters (e.g., pulse duration and amplitude) for programming the desired pulse sequence of oscillating magnetic field $B_1$ to be emitted by the radio frequency coil 51. The test setup routine also interfaces with the waveform generator circuit block 133 to supply the necessary parameters (e.g., gradient pulse timing parameters, gradient pulse amplitude parameter, and gradient pulse waveform duration parameter) for programming the desired pulsed-mode magnetic field gradient $B_{PFG}$ to be emitted by the gradient coil array 67A, 67B.

The NMR measurement routine triggers the electronic circuitry of instrument housing 101 to radiate the sample volume with the desired pulse sequence of oscillating magnetic field $B_1$ in conjunction with the desired pulsed-mode magnetic field gradient $B_{PFG}$ and measures and records the NMR resonance signals (e.g., including resonance spin echoes) that result therefrom.

The NMR data analysis module processes the NMR data recorded from one or more suites of NMR measurements carried out by the NMR measurement module to characterize NMR-related parameters (e.g., $T_2$, D) as well as other properties of interest (e.g., relative volumes of oil and water, oil viscosity, molecular composition of the oil, and gas-oil ratio) for the core sample of interest, and stores the results of NMR data analysis for the core sample of interest. Such stored results can be output, for example, presented to a user on a display screen.

The NMR measurements carried out by the NMR measurement module measure spin echo amplitude for one or more NMR sequences. From these measurements, the diffusion coefficient D, as well as other fluid properties of the core sample of interest, can be derived. The NMR measurements thus obtained are "diffusion encoded" and can be inverted to produce a multi-dimensional distribution function relating to fluid properties of the core sample of interest. The multi-dimensional distribution can be a two dimensional (2-D) distribution function $f(D,T_2)$ relating the diffusion coefficient D to the spin-spin relaxation times ($T_2$) of the core sample of interest, a 2-D distribution function $f(D,T_1)$ relating the diffusion coefficient D to the spin-lattice relaxation time $T_1$ of the core sample of interest, or a three-dimensional (3-D) distribution function $f(D, T_1, T_2)$ relating the diffusion coefficient D to the spin-lattice relaxation time $T_1$ and the spin-spin relaxation time $T_2$ of the core sample of interest. Examples of such inversion techniques are described in detail in U.S. Pat. Nos. 6,570,382; 6,960,913; and 7,053,611.

The permanent magnet of the apparatus of FIGS. 2 and 3 has an open configuration wherein the permanent magnet is removably disposed within the load frame (internal of the load frame) about the radio frequency coil 51 and the central portion of the vessel 13 of the core holder 11 without the need for depressurization of the core holder 11 and detachment of the load frame from the core holder 11. This open configuration allows the same permanent magnet (and possibly the gradient coil array supported thereon) to be used for NMR analysis of a plurality of core samples without the need for depressurizing the respective core holder and disassembling the respective core holder and corresponding load frame for each core sample.

Figure 4:
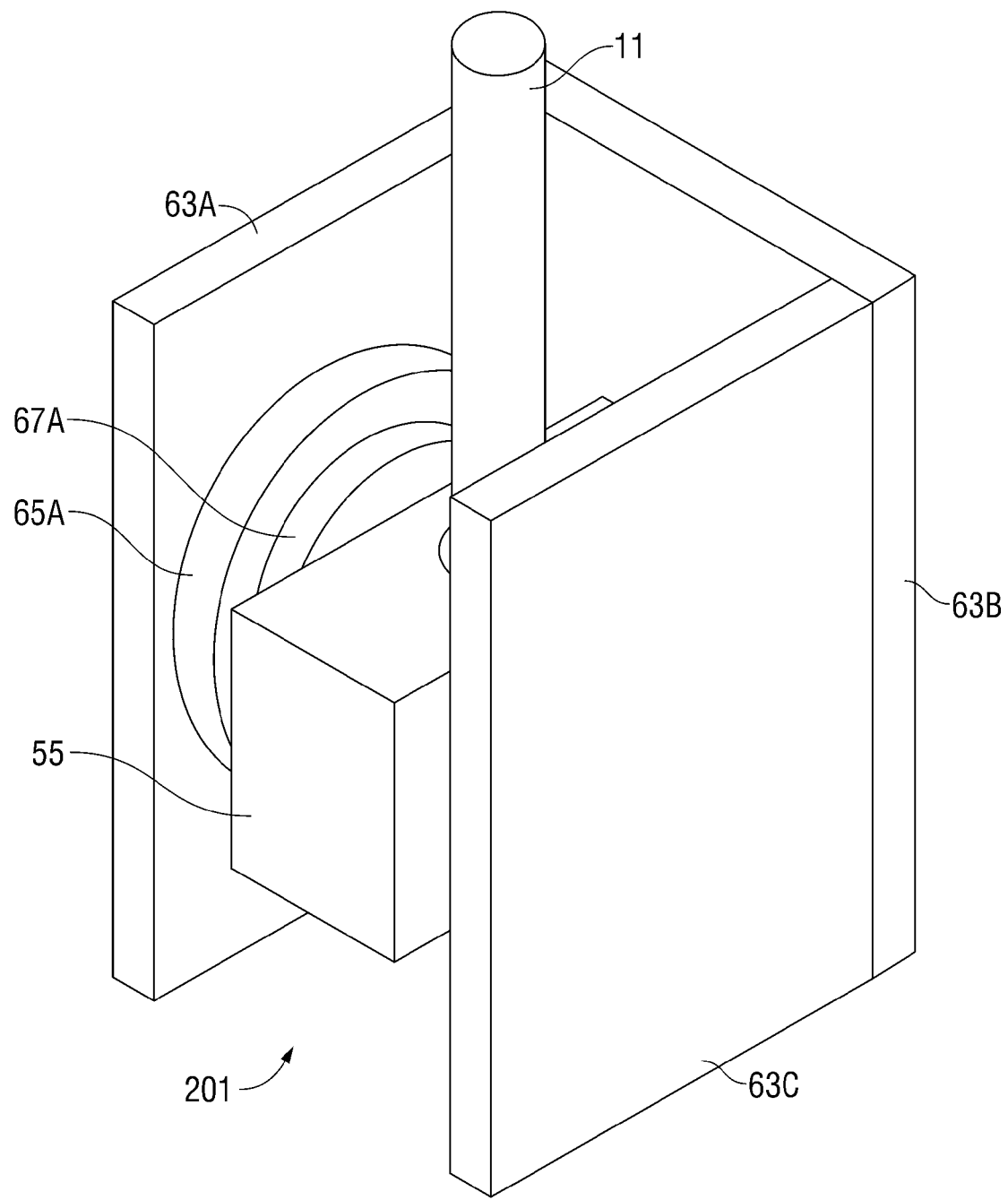
FIG. 4 is a perspective view illustrating an embodiment of the permanent magnet of FIGS. 2 and 3.

In one embodiment of the present application, the permanent magnet of the apparatus of FIG. 2 employs an iron yoke 63 that is generally U-shaped (or possibly C-shaped) as shown in FIG. 4. More specifically, the iron yoke 63 employs three pillars 63A, 63B, 63C that surround the sample volume of the radio frequency coil 51 (which is housed within the enclosure 55 of FIG. 4). The opposed pillars 63A and 63C support the opposed magnet poles 65A, 65B as well as the opposed gradient coils 67A, 67B of the apparatus. Additional permanent magnets can be supported by the pillars of the yoke 63 in order to improve the homogeneity of the static magnetic field $B_0$ over the sample volume. The ends of the opposed pillars 63A and 63C that are opposite pillar 63B define an opening 201 as shown in FIG. 4. The opening 201 is sized to allow for passage of the core holder 11 and enclosure 55 therethrough. This open design allows for removal of the permanent magnet (yoke 63 and magnet poles 65A, 65B) as well as the gradient coil array 67A, 67B supported by the permanent magnet from the assembly of the load frame and the core holder 11 without the need for depressurization of the core holder 11 and detachment of the load frame from the core holder 11. The open design of the yoke 63 can be formed from a single cast of iron or possibly from several pieces that are bolted, welded, or otherwise secured together in a manner that adequately supports the magnet poles and resists the magnetic attraction between the poles.

Figure 5:
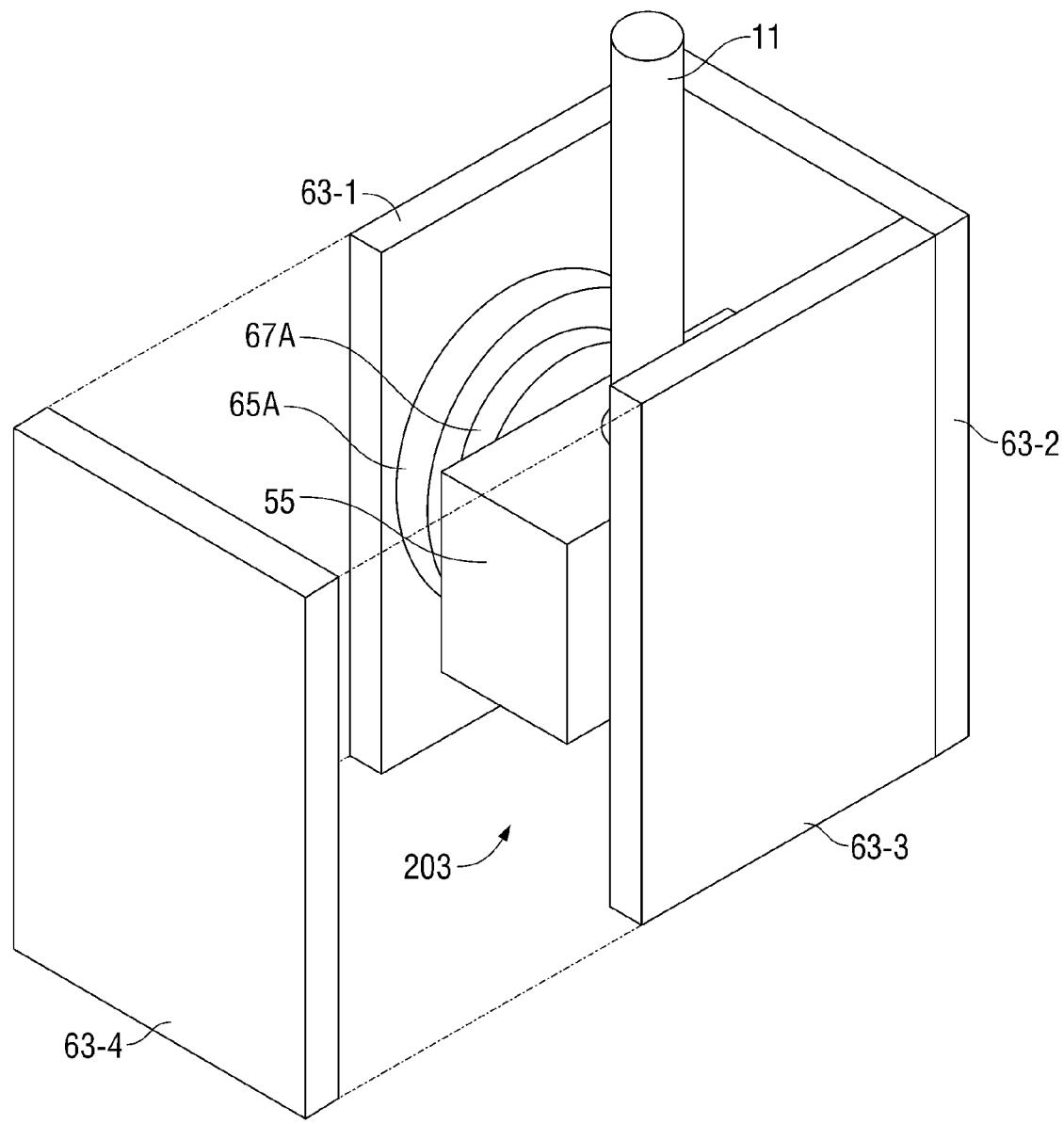
FIG. 5 is a perspective view illustrating another embodiment of the permanent magnet of FIGS. 2 and 3.

In an alternate embodiment of the present application shown in FIG. 5, the permanent magnet of the apparatus of FIG. 2 employs an iron yoke 63 that employs four pillars 63-1, 63-2, 63-3, 63-4. Two opposed pillars 63-1 and 63-3 support the opposed magnet poles 65A, 65B as well as the opposed gradient coils 67A, 67B of the apparatus. One of the other two pillars (such as pillar 63-4 as shown) is detachable and removable from the two opposed pillars 63-1 and 63-3. With pillar 63-4 attached to the two opposed pillars 63-1 and 63-3, the four pillars surround the sample volume of the radio frequency coil 51. With pillar 63-4 detached and removed from the two opposed pillars 63-1 and 63-3, an opening 203 is defined by the ends of the two opposed pillars 63-1 and 63-3. Additional permanent magnets can be supported by the pillars of the yoke 63 in order to improve the homogeneity of the static magnetic field $B_0$ over the sample volume. The opening 203 is sized to allow for passage of the core holder 11 and enclosure 55 therethrough. This open design allows for removal of the permanent magnet as well as the gradient coil array 67A, 67B supported by the permanent magnet from the assembly of the load frame and the core holder 11 without the need for depressurization of the core holder 11 and detachment of the load frame from the core holder 11. The open design of the pillars 63-1, 63-2, 63-3 of the yoke 63 can be formed from a single cast of iron or possibly from several pieces that are bolted, welded, or otherwise secured together in a manner that adequately supports the magnet poles and resists the magnetic attraction between the poles.

Figure 6:
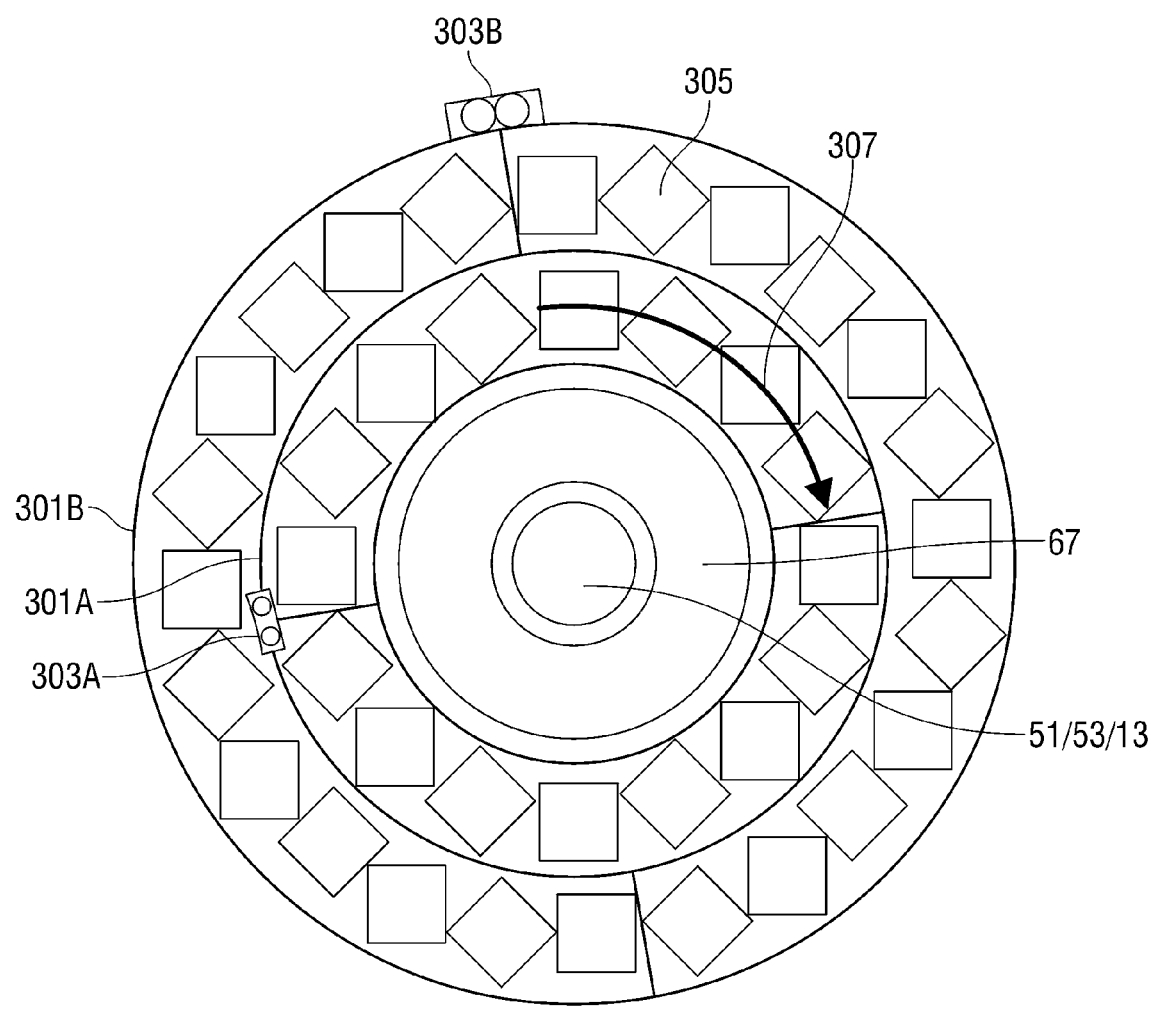
FIG. 6 is a top schematic view illustrating yet another embodiment of the permanent magnet of FIGS. 2 and 3.

In yet another embodiment of the present application, the permanent magnet of the apparatus of FIG. 2 is realized by two cylindrical Halbach-type magnet arrays (an inner cylindrical Halbach-type magnet array 301A and an outer cylindrical Halbach-type magnet array 301B) that can be positioned in a concentric manner relative to one another as shown in FIG. 6. Both the inner and the outer cylindrical Halbach-type arrays include two semi-cylindrical parts that are connected by a respective hinge (303A, 303B) that provides for pivoting movement of the two semi-cylindrical parts about an axis parallel to the central axis of the respective cylindrical array. Both the inner and outer array have many individual magnetic elements 305. With the respective hinges 303A, 303B in their closed configuration (FIG. 6), the inner array 301A is positioned concentrically inside the outer array 301B, and the inner array 301A surrounds the radio frequency coil 51, the cylindrical former 53, and the central portion of the tubular vessel 13 of the core holder 11 shown in FIG. 6. A cylindrical gradient coil 67 is positioned between the inner wall of the inner array 301A and the radio frequency coil 51 and surrounds the radio frequency coil 51 of the apparatus in its assembled configuration. In this design, the cylindrical gradient coil 67 cannot be opened and removed from the core holder 11 and load frame assembly without the need for depressurization of the core holder 11 and detachment of the load frame from the core holder 11. Thus, multiple gradient coils 67 are required, one for each core holder and load frame assembly. By rotating the inner array 301A relative to the outer array 301B (see arrow 307), the strength of the static magnetic field $B_0$ can be reduced. When the static magnetic field $B_0$ is reduced significantly (for example, it can be adjusted to reach 0 T), the two semi-cylindrical parts of the outer array 301B can be pivoted about the hinge 303B into an open configuration that allows for removal of the outer array 301B from the inner array 301A. The two semi-cylindrical parts of the inner array 301A can then be pivoted about the hinge 303A into an open configuration that allows for removal of the inner array 301A from the radio frequency coil 51, the cylindrical former 53, and the central portion of the tubular vessel 13 of the core holder 11 supported therein. The open configurations of the outer array 301B and the inner array 301A thus allow for removal of the permanent magnet arrays 301A, 301B from the radio frequency coil 51, the cylindrical former 53, and the central portion of the tubular vessel 13 of the core holder 11 and load frame assembly without the need for depressurization of the core holder 11 and detachment of the load frame from the core holder 11. Thus, the two cylindrical Halbach-type magnet arrays can be shared for NMR analysis of multiple core holder and load frame assemblies. An example of a dual cylindrical Halbach-type magnet array is described in "A portable Halbach magnet that can be opened and closed without force: the NMR-CUFF", *Journal of Magnetic Resonance*, 208(1), January 2011, pp. 27-33.

In alternate embodiments, the cylindrical gradient coil 67 can be substituted by a gradient coil array supported by the inner wall of the inner array 301A. In this design, the two cylindrical Halbach-type magnet arrays as well as the gradient coil array can be removed from the core holder 11 and load frame assembly without the need for depressurization of the core holder 11 and detachment of the load frame from the core holder 11. Thus, the two cylindrical Halbach-type magnet arrays and the gradient coil array can be shared for NMR analysis of multiple core holder and load frame assemblies.

Figure 7A:
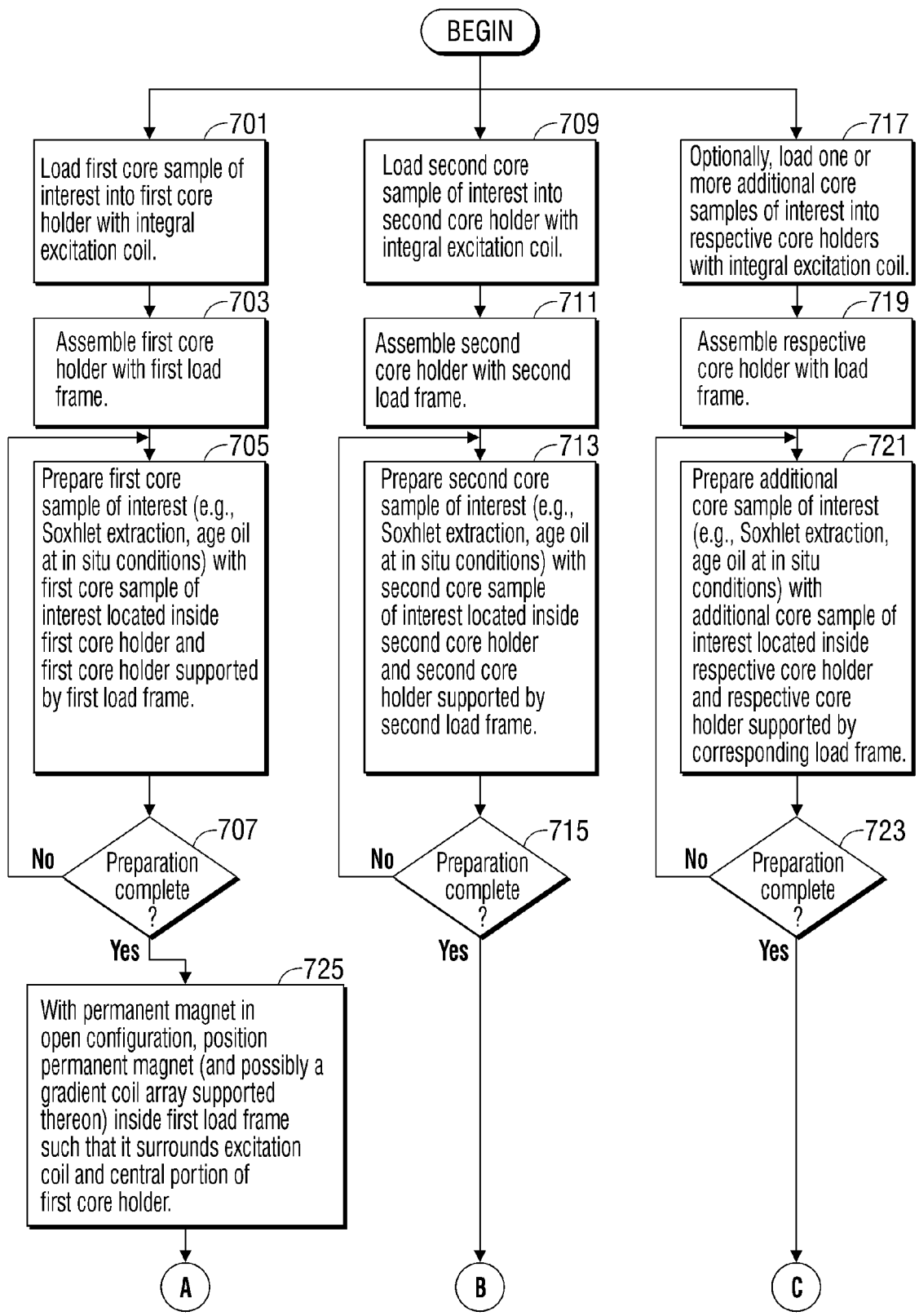
FIGS. 7A-7C, collectively, are a flow chart illustrating operations that use the apparatus of the present application in carrying out NMR measurements for a number of rock core samples of interest.
Figure 7B:
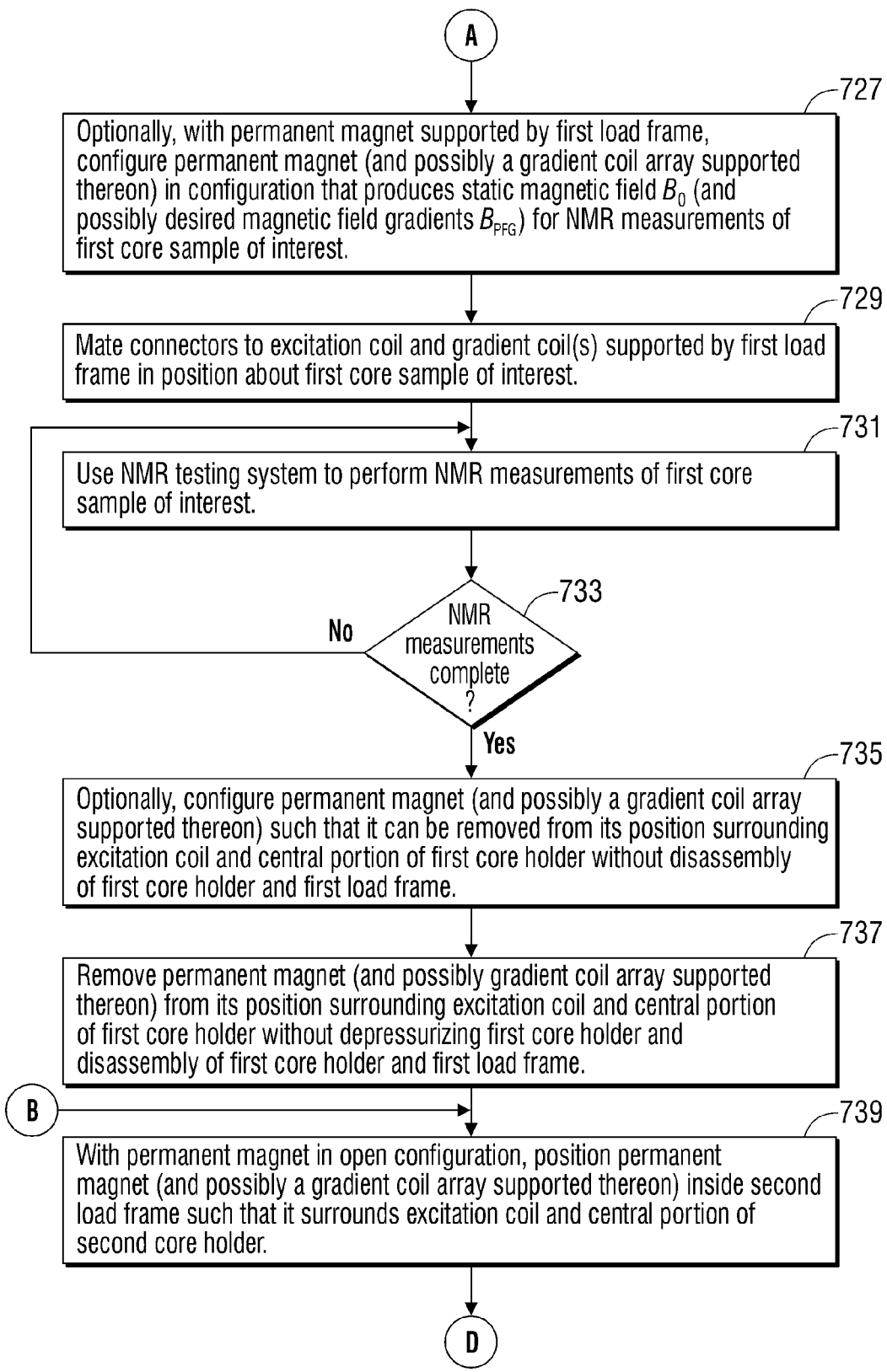
Figure 7C:
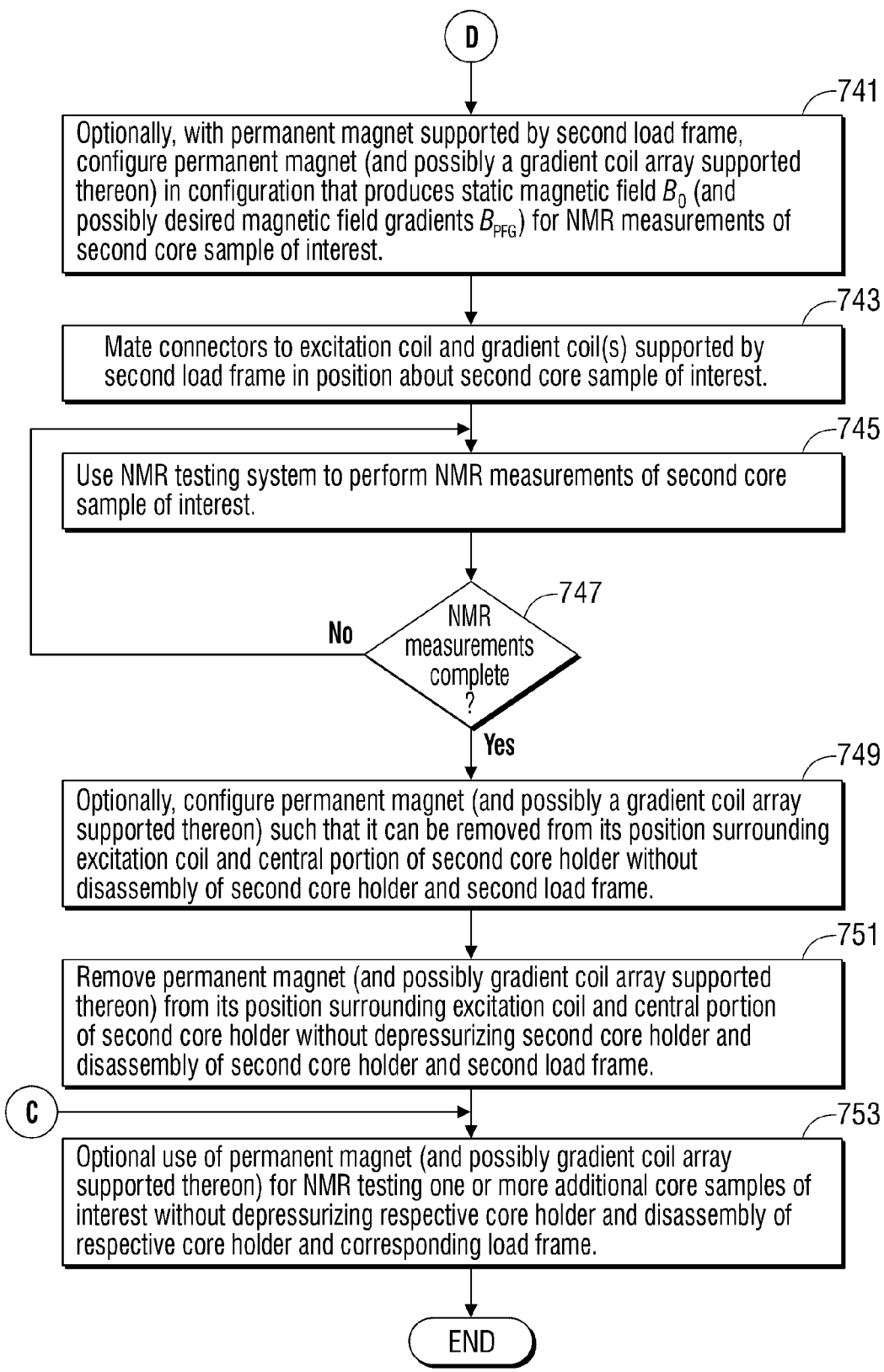

FIGS. 7A-7C, collectively, are a flow chart that illustrates the use of the apparatus of the present application in carrying out NMR measurements for a number of rock core samples of interest.

In step 701, a first core sample of interest is loaded into a first core holder 11 with an integral radio frequency excitation coil 51 (FIG. 2).

In step 703, the assembly of the first core holder 11 and a first load frame (cross-beams 57A, 57B and rods 61A, 61B) is constructed as described above with respect to FIG. 2.

In step 705, the first core sample of interest is prepared for NMR measurements with the first core sample of interest located inside the first core holder and the first core holder supported by the first load frame. Such preparation can involve ageing of oil injected into the first core sample of interest via the fluid inlet and outlet ports 31A, 31B of the first core holder 11 (FIG. 1). The ageing can be carried out at reservoir conditions via control of temperature and pressure of the first core sample of interest via the supply of pressured fluid via the pressure ports of the first core holder 11. The ageing can be carried out for a period of days or weeks as desired to allow the wettability state of the first core sample to be restored to reservoir conditions.

In step 707, it is determined whether the preparation is complete for the first core sample of interest. If not, the operations return back to step 705 to wait for completion. If the preparation is complete at this point, the first core sample of interest is ready for NMR measurements and the operations continue to step 725.

Concurrent with (or possibly subsequent to) the operations of steps 701 to 707, the operations of step 709 to 715 are carried out to prepare a second core sample of interest for NMR measurements.

In step 709, a second core sample of interest is loaded into a second core holder 11 with an integral radio frequency excitation coil 51 (FIG. 2).

In step 711, the assembly of the second core holder 11 and a second load frame (cross-beams 57A, 57B and rods 61A, 61B) is constructed as described above with respect to FIG. 2.

In step 713, the second core sample of interest is prepared for NMR measurements with the second core sample of interest located inside the second core holder and the second core holder supported by the second load frame. Such preparation can involve ageing of oil injected into the second core sample of interest via the fluid inlet and outlet ports 31A, 31B of the second core holder 11 (FIG. 1). The ageing can be carried out at reservoir conditions via control of temperature and pressure of the second core sample of interest via the supply of pressured fluid via the pressure ports of the second core holder 11. The ageing can be carried out for a period of days or weeks as desired to allow the wettability state of the second core sample to be restored to reservoir conditions.

In step 715, it is determined whether the preparation is complete for the second core sample of interest. If not, the operations return back to step 713 to wait for completion. If the preparation is complete at this point, the second core sample of interest is ready for NMR measurements and the operations continue to step 739.

Concurrent with (or possibly subsequent to) the operations of steps 701 to 715, the operations of step 717 to 723 are optionally carried out for one or more additional core samples of interest in order to prepare the one or more additional core samples of interest for NMR measurements.

In step 717, the additional core sample of interest is loaded into a respective core holder 11 with an integral radio frequency excitation coil 51 (FIG. 2).

In step 719, the assembly of the respective core holder 11 and a corresponding load frame (cross-beams 57A, 57B and rods 61A, 61B) is constructed as described above with respect to FIG. 2.

In step 721, the additional core sample of interest is prepared for NMR measurements with the additional core sample of interest located inside the respective core holder and the respective core holder supported by the corresponding load frame. Such preparation can involve ageing of oil injected into the additional core sample of interest via the fluid inlet and outlet ports 31A, 31B of the respective core holder 11 (FIG. 1). The ageing can be carried out at reservoir conditions via control of temperature and pressure of the additional core sample of interest via the supply of pressured fluid via the pressure ports of the respective core holder 11. The ageing can be carried out for a period of days or weeks as desired to allow the wettability state of the additional core sample of interest to be restored to reservoir conditions.

In step 723, it is determined whether the preparation is complete for the additional core sample of interest. If not, the operations return back to step 721 to wait for completion. If the preparation is complete at this point, the additional core sample of interest is ready for NMR measurements and the operations continue to step 753.

With the first core sample of interest ready for NMR measurements, the operations continue to step 725 where the permanent magnet is arranged in an open configuration. In this open configuration, the permanent magnet (and possibly a gradient coil array supported thereon) is positioned inside the first load frame such that it surrounds the excitation coil and the central portion of the first core holder. The open configuration can produce the static magnetic field $B_0$ (and possibly the desired pulsed-mode magnetic field gradients $B_{PFG}$) for NMR measurements of the first core sample of interest. In optional step 727, with the permanent magnet supported by the first load frame, the permanent magnet (and possibly a gradient coil array supported thereon) is arranged in a configuration that produces the static magnetic field $B_0$ (and possibly the desired magnetic field gradients $B_{PFG}$) for NMR measurements of the first core sample of interest.

Examples of the open configuration of step 725 for two U-shaped (or C-shaped) permanent magnet designs are shown in FIGS. 4 and 5. For the U-shaped (or C-shaped) permanent magnet design of FIG. 4, step 727 can be omitted as the open configuration of the magnet provides the desired static magnetic field. For the U-shaped (or C-shaped) permanent magnet design of FIG. 5, step 727 can involve securing the pillar 63-4 to the ends of the two pillars 63-1, 63-3 to close the opening 203. For the dual cylindrical Halbach-type magnet array of FIG. 6, the open configuration of the inner array is obtained by pivoting the two semi-cylindrical portions about the hinge 303A to separate the two semi-cylindrical portions from one another. This open configuration allows the two semi-cylindrical portions to close around the semi-cylindrical portions about the radio frequency coil 51, the cylindrical former 53, and the central portion of the tubular vessel 13 of the first core holder such that the semi-cylindrical portions surround the radio frequency coil 51, the cylindrical former 53, and the central portion of the tubular vessel 13 of the first core holder as shown in FIG. 6. The open configuration of the outer array is obtained by pivoting the two semi-cylindrical portions about the hinge 303B to separate the two semi-cylindrical portions from one another and then close around the inner array (in a rotational orientation with reduced field that allows for closure of the outer array). The outer array can then be rotated relative to the inner array to a rotational orientation that provides the desired static magnetic field. FIG. 6 shows the arrangement of the outer and inner arrays configured for NMR measurements as a result of step 727.

In step 729, the connector 103A is arranged to provide an electrical connection between the NMR measurement apparatus (e.g., T/R matching circuitry 127 of instrument housing 101) and the radio frequency excitation coil 51 supported by the first load frame in a position about the first core sample of interest. Similarly, the connector 103B is arranged to provide an electrical connection between the NMR measurement apparatus (e.g., gradient coil driver circuitry 135 of instrument housing 101) and the gradient coil(s) supported by the first load frame in a position about the first core sample of interest.

In step 731, the NMR measurement apparatus (e.g., programmed computer 171 and instrument housing 101) is used to perform NMR measurements of the first core sample of interest as described above.

In step 733, it is determined whether the NMR measurements of step 731 are complete for the first core sample of interest. If not, the operations return back to step 731 to wait for completion. If the NMR measurements are complete at this point, the operations continue to steps 735 and 737.

In optional step 735, the permanent magnet (and possibly a gradient coil array supported thereon) is configured such that it can be removed from its position surrounding the radio frequency excitation coil 51 and the central portion of the first core holder without disassembly of the first core holder and the first load frame. In step 737, the permanent magnet (and possibly the gradient coil array supported thereon) is removed from its position surrounding the radio frequency excitation coil 51 and the central portion of the first core holder without the need to depressurize the first core holder and disassemble the first core holder and the first load frame.

For the U-shaped (or C-shaped) permanent magnet design of FIG. 4, step 735 can be omitted. For the U-shaped (or C-shaped) permanent magnet design of FIG. 5, step 735 can involve removing pillar 63-4 from the ends of the two pillars 63-1, 63-3 to access the opening 203. For the dual cylindrical Halbach-type magnet array of FIG. 6, the inner array 301A is rotated relative to the outer array 301B (see arrow 307) to reduce the strength of the static magnetic field $B_0$, and the two semi-cylindrical parts of the outer array 301B are pivoted about the hinge 303B into an open configuration that allows for removal of the outer array 301B from the inner array 301A. The two semi-cylindrical parts of the inner array 301A can then be pivoted about the hinge 303A into an open configuration that allows for removal of the inner array 301A from the radio frequency coil 51, the cylindrical former 53, and the central portion of the tubular vessel 13 of the core holder 11 supported therein.

In step 739, the permanent magnet is arranged in an open configuration. In this open configuration, the permanent magnet (and possibly a gradient coil array supported thereon) is positioned inside the second load frame such that it surrounds the excitation coil and the central portion of the second core holder. The open configuration can produce the static magnetic field $B_0$ (and possibly the desired magnetic field gradients $B_{PFG}$) for NMR measurements of the second core sample of interest. In optional step 741, with the permanent magnet supported by the second load frame, the permanent magnet (and possibly a gradient coil array supported thereon) is arranged in a configuration that produces the static magnetic field $B_0$ (and possibly the desired magnetic field gradients $B_{PFG}$) for NMR measurements of the second core sample of interest. The operations of steps 739 and 741 are similar to those of steps 725 and 727 as described above.

In step 743, the connector 103A is arranged to provide an electrical connection between the NMR measurement apparatus (e.g., T/R matching circuitry 127 of instrument housing 101) and the radio frequency excitation coil 51 supported by the second load frame in a position about the second core sample of interest. Similarly, the connector 103B is arranged to provide an electrical connection between the NMR measurement apparatus (e.g., gradient coil drive circuitry 135 of instrument housing 101) and the gradient coil(s) supported by the second load frame in a position about the second core sample of interest.

In step 745, the NMR measurement apparatus (e.g., programmed computer 171 and instrument housing 101) is used to perform NMR measurements of the second core sample of interest as described above.

In step 747, it is determined whether the NMR measurements of step 745 are complete for the second core sample of interest. If not, the operations return back to step 745 to wait for completion. If the NMR measurements are complete at this point, the operations continue to steps 749 and 751.

In optional step 749, the permanent magnet (and possibly a gradient coil array supported thereon) is configured such that it can be removed from its position surrounding the radio frequency excitation coil 51 and the central portion of the second core holder without disassembly of the second core holder and the second load frame. In step 751, the permanent magnet (and possibly the gradient coil array supported thereon) is removed from its position surrounding the radio frequency excitation coil 51 and the central portion of the second core holder without the need to depressurize the second core holder and disassemble the second core holder and the second load frame.

In optional block 753, the permanent magnet (and possibly the gradient coil array supported thereon) can be used for NMR measurements of one or more additional core samples of interest without disassembly of the respective core holder and corresponding load frame. These operations are similar to those described above with respect to steps 739 to 751.

Importantly, the apparatus and methods of the present application allow the same permanent magnet (and possibly the gradient coil array supported thereon) to be used for NMR analysis of a plurality of core samples of interest without the need for depressurizing the respective core holder and disassembling the respective core holder and corresponding load frame for each core sample. In this manner, the apparatus and methods of the present application avoid the expensive costs of using separate permanent magnets (and possibly separate gradient coil arrays) for each core sample of interest, which is currently required for NMR analysis of a plurality of core samples without depressurizing the respective core holder and disassembling the respective core holder and corresponding load frame for each respective core sample. The apparatus and method of the present application also allows multiple core samples to be prepared for NMR analysis with the core samples separated from the permanent magnet and the NMR measurement apparatus.

There have been described and illustrated herein several embodiments of an apparatus (and corresponding method) for nuclear magnetic resonance (NMR) analysis of a plurality of core samples. While particular embodiments of the invention have been described, it is not intended that the invention be limited thereto, as it is intended that the invention be as broad in scope as the art will allow and that the specification be read likewise. Thus, while a particular configuration of a flow-through Hassler-type biaxial core holder has been disclosed, it will be appreciated that other biaxial and triaxial core holders can be used as well. In addition, while a particular configuration of an NMR measurement apparatus (and the operation of such apparatus) has been disclosed, it will be understood that other NMR measurement apparatuses can be used. Moreover, while particular configurations have been disclosed in reference to the open-access configuration of the permanent magnet, it will be appreciated that other suitable open-access configurations could be used as well. It will therefore be appreciated by those skilled in the art that yet other modifications could be made to the provided invention without deviating from its scope as claimed.

What is claimed is:

1. A method for acquiring nuclear magnetic resonance (NMR) measurements of a plurality of subterranean core samples, the method comprising:
   holding a first core sample in a first core holder under pressurized conditions, the first core holder having a first radio frequency coil disposed about a portion of the first core holder, the first radio frequency coil for generating a pulsed-mode magnetic field component over a sample volume occupied by the first core sample;
   removably securing a first support structure to the first core holder, the first support structure providing resistance to forces resulting from the pressurized conditions of the first core holder, and the first support structure allowing for access to interior space surrounding the portion of the first core holder and the first radio frequency coil disposed thereabout;
   removably disposing a permanent magnet into a position within the first support structure about the first radio frequency coil and the portion of the first core holder without the need for depressurization of the first core holder and detachment of the first support structure from the first core holder, the permanent magnet for applying a static magnetic field component to the sample volume occupied by the first core sample for NMR measurements of the first core sample;
   holding a second core sample in a second core holder under pressurized conditions, the second core holder having a second radio frequency coil disposed about a portion of the second core holder, the second radio frequency coil for generating a pulsed-mode magnetic field component over a sample volume occupied by the second core sample;
   removably securing a second support structure to the second core holder, the second support structure providing resistance to forces resulting from the pressurized conditions of the second core holder, and the second support structure allowing for access to interior space surrounding the portion of the second core holder and the second radio frequency coil disposed thereabout;
   removing the permanent magnet from the position within the first support structure about the first radio frequency coil and the portion of the first core holder without the need for depressurization of the first core holder and detachment of the first support structure from the first core holder; and
   after removing the permanent magnet from the position within the first support structure, removably disposing the permanent magnet into a position within the second support structure about the second radio frequency coil and the portion of the second core holder without the need for depressurization of the second core holder and detachment of the second support structure from the second core holder, the permanent magnet for applying a static magnetic field component to the sample volume occupied by the second core sample for NMR measurements of the second core sample.

2. A method according to claim 1, further comprising:
   removing the permanent magnet from the position within the second support structure about the second radio frequency coil and the portion of the second core holder without the need for depressurization of the second core holder and detachment of the second support structure from the second core holder; and
   after removing the permanent magnet from the position within the second support structure, removably disposing the permanent magnet into a position within at least one additional support structure for NMR measurements of an additional core sample.

3. A method according to claim 1, wherein:
   said permanent magnet has an open configuration, the open configuration allowing the permanent magnet to be removably disposed within the first support structure about the first radio frequency coil and the portion of the first core holder without the need for depressurization of the first core holder and detachment of the first support structure from the first core holder, and the open configuration allowing the permanent magnet to be removably disposed within the second support structure about the second radio frequency coil and the portion of the second core holder without the need for depressurization of the second core holder and detachment of the second support structure from the second core holder.

4. A method according to claim 3, wherein:
said permanent magnet includes a U-shaped or C-shaped body that supports two magnet poles, wherein the body defines the open configuration.

5. A method according to claim 4, wherein:
said permanent magnet includes a part that is removably secured to the U-shaped or C-shaped body to reconfigure the permanent magnet in a closed configuration.

6. A method according to claim 3, wherein:
said permanent magnet comprises two cylindrical Halbach-type arrays that are arranged in a concentric configuration during use, said two cylindrical Halbach-type arrays each having two semi-cylindrical portions that are coupled together via a hinge interface, wherein pivoting movement of the two semi-cylindrical portions about the hinge interface permits the two cylindrical Halbach-type arrays to be arranged in the open configuration.

7. A method according to claim 3, wherein:
at least one gradient coil is removably disposed within both the first and second support structures without the need for depressurization of the respective core holder and detachment of the respective support structure from the corresponding core holder.

8. A method according to claim 1, further comprising:
positioning at least one first gradient coil within the first support structure about the first radio frequency coil and the portion of the first core holder, said at least one gradient coil for applying a time varying magnetic field gradient component over the sample volume for NMR measurements of the first sample; and
positioning at least one second gradient coil within the second support structure about the second radio frequency coil and the portion of the second core holder, said at least one gradient coil for applying a time varying magnetic field gradient component over the sample volume for NMR measurements of the second sample.

9. A method according to claim 1, wherein:
said first and second support structures each include at least two beams that extend transverse to the central axis of the respective core holder and at least two rods that extend between the at least two beams in a direction parallel to the central axis of the respective core holder.

10. A method according to claim 1, wherein:
said first and second core holders allow for ageing of oil within the first and second core samples under reservoir conditions for NMR measurements of the first and second core samples under reservoir conditions.

11. An apparatus for acquiring nuclear magnetic resonance (NMR) measurements of a subterranean core sample, the apparatus comprising:
a core holder for holding the core sample under pressurized conditions;
a radio frequency coil disposed about a portion of the core holder, said radio frequency coil for generating a pulsed-mode magnetic field component over a sample volume occupied by the core sample;
a support structure that is removably secured to the core holder, the support structure providing resistance to forces resulting from the pressurized conditions of the core holder, and the support structure allowing for access to interior space that surrounds the portion of the core holder and the radio frequency coil disposed thereabout; and
a permanent magnet for applying a static magnetic field component to the sample volume, the permanent magnet having an open configuration wherein the permanent magnet is removably disposed within the support structure about the radio frequency coil and the portion of the core holder without the need for depressurization of the core holder and detachment of the support structure from the core holder.

12. An apparatus according to claim 11, further comprising:
a connector that is coupled to the radio frequency coil, the connector providing a detachable electrical connection between the radio frequency coil and an NMR measurement apparatus.

13. An apparatus according to claim 11, further comprising:
at least one gradient coil operably disposed within the support structure about the radio frequency coil and the portion of the core holder, the at least one gradient coil for applying a time varying magnetic field gradient component over the sample volume.

14. An apparatus according to claim 13, wherein:
the at least one gradient coil is removably disposed within the support structure about the radio frequency coil and the portion of the core holder without the need for depressurization of the core holder and detachment of the support structure from the core holder.

15. An apparatus according to claim 13, wherein:
the at least one gradient coil is supported on the permanent magnet.

16. An apparatus according to claim 13, further comprising:
a connector that is coupled to the at least one gradient coil, the connector providing a detachable electrical connection between the at least one gradient coil and an NMR measurement apparatus.

17. An apparatus according to claim 11, wherein:
the permanent magnet includes a U-shaped or C-shaped body that supports two magnet poles, wherein the body defines an opening that permits the permanent magnet to be removably disposed in a position within the support structure about the radio frequency coil and the portion of the core holder without the need for depressurization of the core holder and detachment of the support structure from the core holder.

18. An apparatus according to claim 17, wherein:
the permanent magnet includes a part that is removably secured to the C-shaped or U-shaped body to close the opening.

19. An apparatus according to claim 11, wherein:
the permanent magnet comprises two cylindrical Halbach-type arrays that are arranged in a concentric configuration during use, the two cylindrical Halbach-type arrays each having two semi-cylindrical portions that are coupled together via a hinge interface, wherein pivoting movement of the two semi-cylindrical portions about the hinge interface permits the two cylindrical Halbach-type arrays to be to removably disposed in a position within the support structure about the radio frequency coil and the portion of the core holder without the need for depressurization of the core holder and detachment of the support structure from the core holder.

20. An apparatus according to claim 11, wherein:
the support structure comprises at least two beams that extend transverse to the central axis of the core holder and at least two rods that extend between the at least two beams in a direction parallel to the central axis of the core holder, wherein the at least two rods define openings that allow for access to the interior space that surrounds the portion of the core holder and the radio frequency coil disposed thereabout.

21. An apparatus according to claim 11, wherein:
the core holder allows for ageing of oil within the core sample under reservoir conditions for NMR measurements of the core sample under reservoir conditions.

\* \* \* \* \*